United States Patent [19]
Zettler et al.

[11] Patent Number: 5,502,235
[45] Date of Patent: Mar. 26, 1996

[54] SOLVENTLESS PROCESS FOR MAKING 2,6 DIFLUOROBENZONITRILE

[75] Inventors: Mark W. Zettler; Richard E. Tobey; Ronald B. Leng, all of Midland, Mich.

[73] Assignee: DowElanco, Indianapolis, Ind.

[21] Appl. No.: 365,726

[22] Filed: Dec. 28, 1994

[51] Int. Cl.$^6$ .................................................. C07C 253/30
[52] U.S. Cl. ............................................................ 558/425
[58] Field of Search ............................................. 558/425

[56] References Cited

U.S. PATENT DOCUMENTS

| | | | |
|---|---|---|---|
| 3,226,448 | 12/1965 | Gorden et al. | 260/650 |
| 3,290,353 | 12/1966 | Battershell et al. | 260/465 |
| 3,300,537 | 1/1967 | Bennett et al. | 260/649 |
| 4,051,168 | 9/1977 | Fiering | 560/8 X |
| 4,174,349 | 11/1979 | Evans et al. | 568/650 X |
| 4,209,457 | 6/1980 | Fuller | 260/465 G |
| 4,226,811 | 10/1980 | Oeser et al. | 568/937 |
| 4,229,365 | 10/1980 | Oeser et al. | 568/588 X |
| 4,351,777 | 9/1982 | Ramanadin | 260/465 X |
| 4,406,841 | 9/1983 | Nishiyama et al. | 260/465 G |
| 4,642,398 | 2/1987 | Cantrell | 568/937 |
| 4,680,406 | 7/1987 | Fujioka et al. | 456/345 |
| 4,684,734 | 8/1987 | Kaieda et al. | 546/345 |
| 4,704,483 | 11/1987 | Tang et al. | 568/937 |
| 4,780,559 | 10/1988 | Brown et al. | 558/425 |
| 4,849,552 | 7/1989 | Cantrell | 568/938 X |
| 4,868,347 | 9/1989 | Blank et al. | 568/937 |
| 4,927,980 | 5/1990 | Cantrell | 568/937 |
| 4,952,719 | 8/1990 | Maul et al. | 558/425 |
| 4,973,771 | 11/1990 | Cantrell | 568/937 |
| 4,973,772 | 11/1990 | Cantrell | 568/937 |
| 4,978,769 | 12/1990 | Kysela et al. | 558/423 |

FOREIGN PATENT DOCUMENTS 2142018  12/1986  United Kingdom .

OTHER PUBLICATIONS

Chem. Ab. 91:157474j, Halogenated benzonitriles, Ger. Offen. (2,902,877), (Aug. 23, 1979), (p. 614).
Chem. Ab. 115:28855z, Method for preparation of fluorobenzenes, (CS 269,080), (Aug. 31, 1990), (p. 726).
Chem. Ab. 91:157418u, Fluorobenzenes, Ger. Offen. (2,803, 259), (Aug. 2, 1979), (p. 610).
Chem. Ab. 102:203744t, 2,6 Difluorobenzonitrile, Ger Offen. (3,422,936), (Jan. 3, 1985).
Derwent Pub. Ltd., 85–007555/02, 2,6 Di:fluoro–benzonitrile prodn.–by reacting 2,6–di:chloro–benzoitrile with potassium fluoride under pressure in absence of solvent, (DE 3422–936–A), (Jan. 3, 1985).
Chem. Ab. 95:150146c, Process for preparations of fluorinated aromatic compounds, U.K. Pat. Appln. (2,058,067), (Apr. 8, 1981), (p. 618).
Chem. Ab. 99:87839w, Fluorobenzonitriles, JP Kokai (58 35,161), (Mar. 1, 1983), (p. 536).
Chem. Ab. 103:71074h, Fluorobenzonitriles, JP Kokai (60 72,850), (Apr. 24, 1985), (p. 626).
Derwent Pub. Ltd. 85–137812/23, Fluorinated benzonitrile(s) prodn.–by nuclear halogen displacement of corresp. chloro cpds, (J6 0072–850–A), (Apr. 24, 1985).
Chem. Ab. 103:71075j, Fluorobenzonitriles, JP Kokai (60 72,851), (Apr. 24, 1985), (p. 626).
Derwent Pub. Ltd. 85–137813/23, High yield prepn. of fluroinated benzonitrile(s)–by substitution of chlorinated benzonitrile in sulpholane, (J6 0072–851–A), (Apr. 24, 1985).
Chem. Ab. 105:114707c, Fluorobenzene derivatives, JP Kokai (61 07 217), (Jan. 13, 1986), (p. 642).
Chem. Ab. 108:150038f, Preparation of fluuorobenzene derivatives as pharmaceutical and agrochemical itnermediates, JP Kokai (62,114,939), (May 26, 1987), (p. 700).
Derwent Pub. Ltd. 87–183186/26, Fluoro:benzene derivs. prepn.–by reacting benzene cpd. with alkali or alkaline earth metal fluoride in absence of solvent, (J62114–939–A), (May 26, 1987).
Derwent Pub. Ltd. 04165X/03, 2–Fluoro–nitrobenzene prepn.–by heating 2–chloro–nitrobenzene with alkali fluoride in the presence of sulpholane, (DT 2527–044), (Jan. 8, 1976).
Derwent Pub. Ltd. 32537V/29, Nuclear fluorinated benzene cpds prepn.–by reacting ortho–or parachlora or bromonitre–, trifluoromethyl–, carboxy– or cyano–benzene with an alkali metal fluoride in dimethylocetam, (GB 1360–327), (Jul. 17, 1974).
Derwent Pub. Ltd. 29363 E/15, Aromatic fluorine cpd. prepn.–by reacting halo–substd. benzen cpd. with alkali metal fluoride in nitrogen–and/or sulphur–contg. polar solvent mixt, (J5 7038–726), (Mar. 3, 1982).
Derwent Pub. Ltd. 85–066411/11, New 2,4,6–tri:fluoro benzonitrile–intermediate for insecticides, pharmaceuticals or dyestuffs, (J6 0023–358–A), (Feb. 5, 1985).
Derwent Pub. Ltd. 86–109224/17, Fluorinating method to exchange activated halogen in cpd.–uses finely powdered and slurried anhydrous potassium fluoride in inert solvent, (J6 1050–945–A), (Mar. 13, 1986).
Chem. Ab. 109:92451t, Process for the preparation of aromatic fluoro compounds as intermediates for drugs and agrochemicals, JP Kokai (63 39,824), (Feb. 20, 1988), (p. 92460).
Derwent Pub. Ltd. 88–088421/13, High yield prepn. of nucleus fluorinated aromatic cpd. –by treating nuclear halo–aromatic cpd. with alkali metal fluoride in aprotic polar solvent in presence of radical polymerisation inhibitor, (J6 3039–824–A), (Feb. 20, 1988).

(List continued on next page.)

*Primary Examiner*—Joseph Paul Brust
*Attorney, Agent, or Firm*—Andrea T. Borucki; Richard T. Knauer

[57] ABSTRACT

A process for making 2,6-difluorobenzonitrile, comprising reacting 2,6-dichlorobenzonitrile with a substantially anhydrous metal fluoride at a temperature between about 160° C. and about 300° C. and in the presence of a phase transfer catalyst, which is typically a polyether, tetra-substituted phosphonium salt, tetra-substituted ammonium salt, and cryptand, but in the absence of a solvent. After taking off the product the resulting mixture may be recycled into the reactor for the next reaction cycle. Upon build-up of tars in the reaction process, the invention includes the separation of catalyst from the tars and the recycle thereof.

25 Claims, No Drawings

OTHER PUBLICATIONS

Chem. Ab. 93:185924r, Fluorination of aromatic compounds, JP Kokai (80 10,573), (Mar. 17, 1980), (p. 185933).
Chem. Ab. 95:168830f, Fluorobenzonitrile derivatives, JP Kokai (81 79,660), (Jun. 30, 1981), (p. 168834).
Derwent Pub. Ltd. 87852 D/48, Fluoro–benzonitrile derivs. mfr.–by reacting nitro–benzonitrile with Gp/I metal fluoride non–protonic polar solvent, (J5 6079–660), (Jun. 30, 1981).
Chem. Ab. 115:135672j, Preparation of fluorinated nitro-or cyanobenzenes, JP Kokai (03 77,850), (Apr. 3, 19910, (p. 936).
Derwent Pub. Ltd. 87–348626/49, Fluoro:benzonitrile from chloro:benzonitrile and potassium fluoride—in a dipolar aprotic solvent, esp. an amide, (WO 8707–267–A), (Dec. 3, 1987).
Derwent Pub. Ltd. 89–288569/40, Polymers, for use as catalysts—contg. ammino–pyridinium salts, used for prepn. of fluorine–contg. aromatic cpds. for medicine and agriculture, (JO 1210–403–A), (Aug. 24, 1989).
Derwent Pub. Ltd. 91–143169/20, Fluorinated nitro or cyano–benzene prepn. for pharmaceutical prod.–by reacting fluorinated nitro or cyano–benzene with potassium fluuoride in presence of cyano pyridine, (JO 3077–850–A), (Apr. 3, 1991).
Derwent Pub. 85–027850/05, Penta:fluoro:benzo:nitrile prodn. from penta:chloro:benzo:nitrile—by two–stage fluorination with powdered alkali metal fluoride in aprotic polar solvent, (J59222463–A), (Dec. 14, 1984).
Derwent Pub. Ltd. 85–137812/23, Fluorinated benzonitrile(s) prodn—by nuclear halogen displacement of corresp. chloro cpds., (J6 0072–850–A), (Apr. 24, 1985).
Derwent Pub. 85–137813/23, High yield prepn. of fluorinated benzonitrile(s)—by substitution of chlorinated benzonitrile in sulphone reaction of chlorinated benzonitrile in sulpholane, (J60072851), (Apr. 24, 1985).
Derwent Pub. 86–275572/42, High yield tetra:fluor:phthalonitrile prepn.—comprises halogen–exchange reaction of tetra:chloro:phthalonitrile in benzonitrile solvent, (J61200955–A), (Sep. 5, 1986).
Derwent Pub. 88–088421/13, High yield prepn. of nucleus fluorinated aromatic cpd.—by treating nuclear halo–aromatic cpd. with alkali metal fluoride in aprotic polar solvent in presence of radical polymerisation inhibitor, (J63039824–A), (Feb. 20, 1988).
Derwent Pub. 83–05838 K/03, Prepn. of aromatic fluoro cpd. from aromatic chloro–or bromo cpd.—by subjecting to halogen exchange in presence of potassium fluoride, alkali(ne earth) fluoride and crown cpd., (J5 7197–226), (Dec. 3, 1982).
Derwent Pub. 94–128801/16, Prepn. of 3,4–di:fluoro:benzonitrile, with by–prod mono:fluoro:benzonitrile controlled—comprises reacting 3–chloro–4–fluuoro:benzonitrile with alkali metal fluoride, (JP06072980–A), (Aug. 26, 1992).
Derwent Pub. 70–55060R, Benzyl cyanides and their homologues suitable for producing pharmaceutically, GB1200970–A), (Aug. 5, 1970).
Derwent Pub. 90–048356, Polymer–fixed amino pyridinium salt derivs.–useful as catalyst for fluoridation of haolgenated aromatic cpds., (JP 0200174 A) (Jan. 8, 1990).
Derwent Pub. 91–152198/21, Polymer–fixed tetrekis:eryl:phosphenium salt dertv.–prepd. by reacting halogenated aromatic cpd. with alkali metal fluoride using salt deriv. as catalyst, (JO 3086–704–A), (Apr. 11, 1991).
Derwent Pub. 87–206270/29, Fluoro:aromatic cpds. prepn. from chloro:aromatic cpds.–by halogen exchange using N–branched alkyl–4 substd, amino–pyridinium halide phase transfer catalyst, (WO 8704–150–A), (Jul. 16, 1987).
Derwent Pub. 86–024690/04, Aromatic fluorine cpds prepn—by substituting chlorine for nitro gp of aromatic cpd. then reacting with metal fluoride in presence of phase–transfer catalyst, (J6 0246 326–A), (Dec. 6, 1985).
Chem. Ab. 114:246929x, Fluorination of aromatic halohydrocarbons, JP Kokai (02,273,626), (Nov. 8, 1990).
Derwent Pub. 90–379461/51, Halogenated aromatic cpds. fluorination—by allowing halogenated cpd. having halogen other than fluorine at the benzene nucleus react with alkali metal fluoride, (JO2273626–A), (Nov. 8, 1990).
Derwent Pub. 84–245112/40, Organo–fluorine cpds. from organo–chlorine or bromine cpds.—by halogen exchange with metal fluoride in benzo nitrile on heating, J9 2004–309–B, (Jan. 27, 1992).
Derwent Pub. 92–041474/05 Chloro–fluoro–nitro–and di:fluoro–nitro–benzene s) prepn.—by reacting excess di:chloro–nitro benzene with alkali metal fluoride using quat. ammonium or phosphonium salt, crown ether, etc., (WO 9200–270–A), (Jan. 9, 1992).
Derwent Pub. 33738 K/14, Fluoro:benzonitrile cpd. prodn. from corresp. chloro cpd.—by reaction with potassium fluoride in 1,3 di:methyl-2–imidazolidinone as solvent, gives high yields, (J5 8035–161), (Mar. 1, 1983).
Derwent Pub. 87852 D/48, Fluoro–benzonitrile derivs. mfr.—by reacting nitro–benzonitrile with Gp/I metal fluoride non–protonic polar solvent, (J5 6079–660), (Jun. 30, 19981).
Derwent Pub. 87–348626/49, Fluoro:benzonitrile from chloro:benzonitrile and potassium fluoride—in a dipolar aprotic solvent, esp. an amide, (WO 8707–267–A), (Dec. 3, 1987).
Derwent Pub. 85–007555/02,2,6–Difluoro–benzonitrile produn. by reacting 2,6–dichloro–benzonitrile with potassium fluoride under pressure in absent of solvent, (DE 3422936–A), (Jan. 3, 1985).
Derwent Pub. 89–059218, Aromatic fluorine cpds.–obtd. by reacting halo–aromatic cpd. with alkali metal fluoride using quat. ammonium or phosphonium salt etc., (JP 01013037–A), (Jan. 17, 1989).
Derwent Pub. 74–52537v, Nuclear fluorinated benzene cpds. prepn.–by reacting ortho or para–chloro or bromonitro–, carboxy- or cyano–benzene with an alkali metal fluoride in dimethylacetam, (GB 1360327–A), (Jul. 17, 1974).
CA 112:57084r, Polymer–supported aminopyridinium salts as catalysts for manufacture of fluoroaromatic compounds, (JP Kokai 01,210,403), (Aug. 24, 1989).

SOLVENTLESS PROCESS FOR MAKING 2,6 DIFLUOROBENZONITRILE

FIELD OF THE INVENTION

This invention relates to a process for making 2,6-difluorobenzonitrile by reacting 2,6-dichlorobenzonitrile with a substantially anhydrous metal fluoride in the absence of a solvent, but in the presence of a phase transfer catalyst, and to a process wherein the catalyst is recovered and recycled.

BACKGROUND OF THE INVENTION

The 2,6-difluorobenzonitrile is a useful intermediate in various industries, particularly in the agricultural chemicals industry. In making the intermediate, numerous processes have been employed. UK Patent 2 142 018 B to Ishihara Sangyo Kaisha Limited discloses reacting 2,6-dichlorobenzonitrile with potassium fluoride in the absence of solvent at 200° to 450° C. under pressure. More specifically, the Ishihara Patent discloses employing at least 21.5 kg/cm$^2$ of pressure. In addition to not employing a solvent, the process disclosed by Ishihara does not employ a catalyst. Japanese Patent Publication #87-114,939, Derwent Publication #87-183186126 to Sumitomo Chem. Industries, discloses reacting a benzonitrile with an alkali metal fluoride and an alkaline earth metal fluoride in the absence of a solvent and at a temperature between 100° to 250° C.

Japanese Patent 90-004,580, Derwent Publication #83-05838K/03 to Dainippon Ink Chemical, discloses a process for preparing p-fluoronitrobenzene by reacting a mixture of KF and an alkali metal fluoride (other than KF) or an alkali earth metal fluoride with a crown ether catalyst and p-chloronitrobenzeneo. Japanese Patent Publication No. 89-1013, 037, Derwent Publication. #89-059218/08 to Ihara Chemical Industries, discloses preparing a halogenated aromatic compound with an alkali metal fluoride using a mixture of catalysts. The mixture of catalysts comprises a quaternary ammonium salt and/or a quaternary phosphonium salt and a crown ether and/or a polyalkylene glycol.

U.S. Pat. No. 4,226,811 to Bayer Aktiengesellschaft claims a process for preparing an aromatic ring-fluorinated compound by reacting a substituted chlorobenzene with potassium fluoride in the presence of a crown ether catalyst and a solvent. U.S. Pat. No. 4,978,769 to Bayer Aktiengesellschaft claims a process for preparing an aromatic fluorinated compound by nucleophilic exchange between an educt, such as 2,6-difluorobenzonitrile and KF in the presence of a phase transfer catalyst and a salt of a metal of main groups 3 to 5 of the periodic table of elements and of sub-group elements. Examples of such salts could include chromium salts (CrCl$_3$x6H$_2$O), iron salts (FeCl$_3$), cobalt salts (CoCl$_2$x6H$_2$O), zinc salts (ZnCl$_2$) and antimony salts (SbCl$_3$).

U.S. Pat. No. 3,300,537 to Bennett which was assigned to The National Smelting Company discloses a process for converting halogen aromatic rings that do not contain an activating group such as nitro to a fluorinated aromatic compound. This reaction is conducted with a dry alkali metal fluoride at very high reaction conditions of between 300° C. to 700° C. without using a solvent or catalyst at high pressures.

In view of the previous process, it is highly desirable to have a process that would produce high yields, is environmentally preferred, but is economical. One of the problems with employing crown ether catalyst as described above is that they are extremely expensive, thereby making the processes not economical for commercial production.

SUMMARY OF THE INVENTION

The invention relates to a process for making 2,6-difluorobenzonitrile (hereinafter DFBN). DFBN is made by reacting 2,6-dichlorobenzonitrile (hereinafter DCBN) with a substantially anhydrous metal fluoride at a temperature between about 160° C. and about 300° C. The reaction is conducted in the presence of a phase transfer catalyst. The phase transfer catalyst is typically a polyether, tetra-substituted phosphonium salt, tetra-substituted ammonium salt, or cryptand.

The anhydrous metal fluoride can be prepared by azeotropic distillation of the reaction mixture in vacuo, oven drying at high temperatures, spray drying or a combination of the techniques. The advantages to drying the metal fluoride in the absence of a solvent, which tend to be hygroscopic and difficult to dry. Another advantage to not using a solvent is that no product/solvent separation is needed. The metal fluoride can be sodium fluoride, cesium fluoride, potassium fluoride, rubidium fluoride or cuprous fluoride, with potassium fluoride being preferred. Polyethers are preferably employed as the catalyst, with the crown ethers being the most preferred type of polyether.

One intermediate of the reaction is 2-chloro-6-fluorobenzonitrile (hereinafter CFBN). CFBN may be recycled into subsequent reactions as part of an ongoing manufacturing process. The conversion from DCBN to DFBN not only produces CFBN as an intermediate, but there may be unreacted DCBN and tars (i.e., biaryl ethers) in the resulting reaction product mixture.

Upon completion of the halide exchange reaction, the unreacted metal fluoride salt and metal chloride salt may be separated via filtration or more preferably by extraction with water. The resulting metal fluoride/metal chloride brine is then decanted from the organic phase and can be passed through a steam stripping apparatus for the purpose of recovering any residual volatile organics. The DFBN from the product mixture may then be separated from the reaction product mixture by using vacuum distillation techniques. After the desired DFBN is removed from the reaction product mixture, the resulting mixture containing CFBN, unreacted DCBN, catalyst, tars and any residual DFBN may be recycled back into the reactor (a second mixture). The overall process may be repeated as is needed.

The DCBN, CFBN and any remaining DFBN may be separated and recycled to produce a third mixture comprising the tars and the catalyst. Depending upon the nature and value of the catalyst used, the catalyst may be recovered by adding the mixture to a solvent such as an alcohol, organic aromatic or nitrile solvent, and filtering the resulting insoluble catalyst. Other separation techniques may also be used to recover some catalysts, such as steam stripping and distillation.

DETAILED DESCRIPTION OF THE INVENTION

The invention relates to a process for making 2,6-difluorobenzonitrile (hereinafter DFBN). According to the invention, DFBN is made by reacting 2,6-dichlorobenzonitrile (hereinafter DCBN) with a substantially anhydrous metal fluoride. Typically, this halogen exchange reaction is conducted at a temperature between about 160° C. and about 300° C. at about ambient pressure. The reaction is conducted in the presence of a phase transfer catalyst. By the use of the phrase "phase transfer catalyst" herein, it is meant to be a catalyst that increases the concentration of the fluoride in the organic phase. The phase transfer catalyst is typically selected from the group consisting of polyethers, tetra-substituted phosphonium salt, tetra-substituted ammonium salt, and cryptand. The polyethers are typically crown ethers or linear polyethers.

The anhydrous metal fluoride can be prepared by azeotropic distillation of the reaction mixture in vacuo at about 110° C. Other techniques, such as oven drying in vacuo at high temperatures or spray drying or a combination of the techniques may be used for drying the metal fluoride. The metal fluoride is dried such that the mixture contains less than 0.1 percent by weight water, more preferably less than 0.05 percent, and most preferably less than 0.01 percent by weight water. The metal fluoride can be sodium fluoride, cesium fluoride, potassium fluoride, rubidium fluoride or cuprous fluoride, with potassium fluoride being preferred.

Polyethers are preferably employed as the catalyst, with the crown ethers being the most preferred type of polyether. The 18-crown-6 ethers are the preferred crown ethers. The dibenzo-18-crown-6 crown ether is the most preferred type of 18-crown-6 ether, which is available from Parish Chemicals of Orem, Utah. Other 18-crown-6 ethers may also be used as the catalyst, as well as other polymer supported or nonsupported polyethers. The ammonium salts may be chloride or bromide salts. The ammonium salt is generally phenyl trimethyl ammonium chloride, tetrapentylammonium bromide, Aliquat 336 which is known as 1-octanaminium: N-methyl-N,N-dioctil- chloride or trioctylmethylammonium chloride, dodecyltrimethylammonium bromide, tetradecyltrimethylammonium bromide, or Arquad 16/60 which is known as hexadecyltrimethylammonium bromide. The phosphonium salts may be chloride or bromide salts. The phosphonium salts employed are typically 1-naphthylmethyl triphenyl phosphonium chloride, methoxymethyl triphenyl phosphonium chloride, 4-nitrobenzyl triphenyl phosphonium chloride and tetraphenyl phosphonium chloride. The cryptands with a 6-heteroatom crown system may also be used.

To form DFBN, about 1 mole of DCBN is reacted with about 1 to about 3 mole-equivalents of metal fluoride and about 0.001 to about 0.5 mole-equivalents of catalyst. More preferably, about 1 mole of DCBN is reacted with about 1.5 to about 2.5 mole-equivalents of metal fluoride and about 0.01 to about 0.1 mole-equivalents of catalyst. Most preferably, about 1 mole of DCBN is reacted with about 1.8 to about 2.2 mole-equivalents of metal fluoride and about 0.01 to about 0.06 mole-equivalents of catalyst.

The reaction is typically carried out at between about 160° C. and about 300° C., more preferably about 190° C. to about 260° C., and most preferably at about 225° C. The ammonium and phosphonium salts may be unstable at the higher temperatures discussed herein. Therefore, typically the temperature of the reactions are not greater than about 180° C. when using these salts as catalysts; however as can be seen in the Examples, higher temperatures can be used. The reaction time is typically between about 1 and about 30 hours, preferably between about 10 and about 24 hours. The reaction is typically conducted at about ambient pressure, although higher pressures may be employed if desired. The boiling point of the reaction mixture is typically between about 200° C. to about 235° C., but may decrease as the reaction proceeds. Therefore, when operating at the higher temperatures disclosed herein, the reaction may be operating above ambient pressure. This is particularly true if the reaction is conducted in a closed vessel.

In the reaction, an intermediate 2-chloro-6-fluorobenzonitrile is produced. Reaction yields to DFBN and CFBN are based on consumed DCBN and are between about 90 and about 100 percent, typically between about 95 and about 98 percent. CFBN and any residual DFBN may be recycled into subsequent reactions as part of an ongoing manufacturing process. The conversion from DCBN to DFBN not only produces CFBN as an intermediate, but there may be unreacted DCBN and tars (i.e., biaryl ethers) in the resulting reaction product mixture.

In addition to the techniques discussed above for drying the metal fluoride, another option is to combine the catalyst, DCBN, metal fluoride, and a benzonitrile compound selected from the group consisting of DFBN, CFBN and mixtures thereon in a reactor and to slowly heat the mixture to reflux in vacuo. The temperature is typically not greater than about 130° C. in vacuo. Although the length of time of heating the mixture is not critical, typically the mixture is heated over a period of about 0.1 to about 24 hours, preferably between about 1 and about 10 hours. The temperature is maintained for between about half an hour to about 24 hours, preferably between about 1 to about 10 hours, while distilling up to about 75 weight percent of all of the DFBN and/or CFBN compounds present in the reactor. Generally, vacuum distillation is used to remove the benzonitrile compounds at as low a pressure as is practical, typically at an absolute pressure of about 20 mm Hg. After the drying operation, the temperature of the resulting mixture is then increased to between about 160° C. and about 300° C. so that the halogen exchange reaction proceeds as described above. Alternatively, the catalyst and DCBN can be added to the reactor after the metal fluoride is dried as previously described.

The reaction product mixture may be filtered to removed unreacted metal fluoride salts and any other by-product salts. Preferably, the reaction product mixture is washed with water to remove these salts. This aqueous washing step typically takes place at about 70° C. although temperatures of about 35° C. to about 100° C. could be used. The resulting metal fluoride/metal chloride brine is then decanted from the organic phase and can be passed through a steam stripping apparatus for the purpose of recovering any residual volatile organics.

It is preferred to further reduce the entrained salts in the organic phase following the above aqueous washing operation to prevent the entrained metal fluoride from causing further tar formation during recovery of the product. The entrained salts may be removed by a second water wash. The preferred method of reducing the entrained salts in the organic phase is to utilize a 2 stage, counter current extraction of the washed reaction product mixture to limit the salt content in the organic phase to less than about 0.5 weight percent. An additional benefit to lowering the salt content will be to minimize the corrosion of any stainless steel equipment used in the manufacturing process.

The DFBN may then be separated from the washed or unwashed reaction product mixture by using vacuum distillation techniques. Again, the pressure is maintained at as low a pressure as is practical, typically at an absolute pressure of about 20 mm Hg. The vacuum is maintained for a time between about 1 and about 12 hours, typically for a time of about 8 hours. The temperature is maintained between about 150° C. and about 90° C. during this time, typically at about 110° C.; however, if the reaction product mixture is unwashed, then the temperatures may be as high as 230° C. After the desired amount of DFBN is removed from the reaction product mixture, the resulting mixture containing CFBN, unreacted DCBN, residual DFBN, catalyst and tars may be recycled back into the reactor. This cycle may be repeated until a tar purge is desired.

Because the preferred catalysts are expensive, when employing these materials it is preferred to use a catalyst recovery system. It is also preferred to at least periodically purge the resulting tars from the reactor because they build up over time. The invention therefore includes separating DFBN from the reaction product mixture to produce a second mixture comprising CFBN, unreacted DCBN, the catalyst and the tars resulting from the reaction, and separating DCBN and CFBN from the second mixture to produce a third mixture comprising the tars and the catalyst, and recycling the separated DCBN and CFBN into the reactor.

The DCBN and CFBN are typically separated from the second mixture by using either vacuum or steam distillation (steam stripping) techniques. Preferably vacuum distillation techniques are used for the separation. Because the distillation of DCBN can be inefficient, it is desirable to react the DCBN as far to completion as possible before commencing the tar purge and catalyst recovery operation. If steam distillation is used, the resulting water phase is decanted from the resulting organic phase and may then be passed through a bed of activated carbon to remove any organics remaining in the water phase before being discarded. When steam distillation is employed, a minimum boiling, heterogeneous azeotrope exists, which generally permits the steam distillation to take place at about atmospheric pressure and about 100° C. After the steam stripping operation is completed, the organic phase at the bottom of the stripping vessel may be difficult to decant from the water phase because the organic phase typically has a freezing point very close to about 100° C. Optionally, an efficient flux solvent such as biphenyl phenyl ether (hereinafter BIPPE) may be used to make the organic phase less viscous. The use of a flux solvent makes decantation operations easier to complete.

A second method of recovering unreacted DCBN and CFBN from the tars and catalyst is to perform a vacuum distillation in the presence or absence of a flux solvent. The key advantage of using vacuum distillation rather than steam distillation is that a relatively cool decantation of a viscous liquid or semi-solid organic phase from water is avoided. The major drawback is that a very low volume organic phase is produced at the end of the vacuum distillation, unless a flux solvent is used. In performing the vacuum distillation, a low volume reboiler capable of operating at temperatures greater than about 235° C. is typically used. The vacuum distillation is typically conducted at about 250° C. and at as low a vacuum as is practical, e.g., at about 20 mm Hg absolute pressure. A hot condenser may be used if DCBN is present in relatively large quantities; otherwise, a condenser capable of operating at temperatures greater than about 65° C. would likely be sufficient to prevent CFBN from freezing. The vacuum distillation apparatus preferably comprises a column drainback leg or trap to prevent DCBN and CFBN losses to the tars.

Depending on the value of the catalyst selected and the economics of recovering it, recovery options include steam stripping, extraction, distillation and filtration methods. The catalyst may be recovered from the third mixture containing tars (and the flux solvent if used) by steam stripping and then distillation. A preferred technique is to dissolve the tars and flux solvent in a suitable solvent and recovering the insoluble catalyst by filtration. Due to the fact that some ammonium or phosphonium catalysts are readily available and are inexpensive, the catalyst need not be not recovered from the catalyst and tar mixture, but instead the mixture is typically discarded.

The tars may be dissolved in an alcohol, organic aromatic or nitrile solvent, such as methanol, acetone, acetonitrile, toluene and chlorobenzenes. The solvent is preferably methanol. Solvent to tar weight ratios of about 5:1 to about 20:1 can be used, with a ratio of about 10:1 being typically used. The tar extraction step can be carried out at a temperature between the freezing point and the boiling point of the solvent, although the tar extraction is typically conducted at moderate temperatures, e.g., about 20° C.

The solvent dissolves the tars and the flux solvent, but the catalyst precipitates out of the solvent. The catalyst can then be recovered using well-known filtration techniques. Such techniques could include but are not limited to centrifuges and pressure or vacuum filters. Suitable filtration devices include tubular, horizontal or vertical leaf, or nutsch type filters having a capacity of about 25 ft$^3$ and having cake (recovered precipitate) washing capability. The recovered catalyst is typically washed with an organic solvent and water, dried, and then recycled into the reactor. If desired, the recovered catalyst can be recovered from the filtration device by dissolving the catalyst in a warm (e.g., at least about 60° C.) stream of DFBN, DCBN, CFBN, or a combination thereof, and then recycling the dissolved catalyst stream into the reactor. The solvent not only dissolves the tars but also acts as a diluent to reduce the fluoride concentration in the tar stream which is appropriately discarded.

EXAMPLES

Example 1- PART A: Fluorination of DCBN with KF 230g (165mL)(d=1.40) of DFBN, 203g (3.5 moles) of dry KF and 285g (1.66 moles) of DCBN were charged to a 1000 mL 4-necked round bottom glass flask and the contents were heated. The flask was equipped with a condenser, a mechanical stirrer and a thermowell. The condenser was installed between the reactor (the flask) and a nitrogen source. As the KF was added to the DFBN and DCBN, the reaction mixture became unstirrable until the temperature reached 140° C. The pot was heated to 150° C. At the start of the reaction, the concentration of DCBN was 55.3 weight percent (hereinafter wt. %). The DFBN concentration was 44.7 wt. %. There was no indication that the reaction was proceeding since the concentration of the DCBN did not change in 1.5 hours. At this time, 3g of tris(dioxa3,6-heptyl)amino phase transfer catalyst was added. The pot temperature was increased to 170° C. After 24 hours of reaction time, the DCBN concentration was 45 wt. %, the CFBN concentration was 8 wt. %, and the DFBN product concentration was 45 wt. %. After 48 hours of reaction time, the DCBN concentration was 40 wt. %, the CFBN concentration was 13 wt. % and the DFBN product concentration was 48.7 wt. %. 2g of 18-crown-6 catalyst was then added. After 72 hours of reaction time, the DCBN concentration was 18 wt. %, the CFBN concentration was 27 wt. %, and the DFBN product concentration was 51 wt. %. Since the reaction was progressing slowly, an additional 2.8g of 18-crown-6 catalyst was added. At 96 hours of reaction time, the DCBN concentration was 1 wt. %, the CFBN concentration was 16 wt. %, and DFBN product concentration was 80 wt. %. At 120 hours of reaction time, the starting material was reacted, the CFBN concentration was 7 wt. %, and DFBN product concentration was 89 wt. %. At 146 hours of reaction time, the CFBN concentration was 3 wt. %, and DFBN product concentration was 93 wt. %. At 150 hours of reaction time, the CFBN concentration was 2 wt. %, and DFBN product concentration was 97 wt.

%. The reaction product mixture was allowed to cool to 55° C., 1100 mL of water was added, and the mixture was phase-separated. The resulting salt solution (brine) had a concentration of 14 wt. %. The washed product was 457.5g of 96.4 wt. % DFBN, the calculated yield was 460g, 95.8 % yield based on DCBN starting material and DFBN product that was fed PART B: Steam Distillation of DFBN product Most of the product from Part A (453g of 96.4 wt. % DFBN) was charged to a 1 liter 4-necked round bottom flask. The flask was equipped with a short vigreaux column, condenser, receiver steam tube and a thermowell. The receiver was cooled in an ice/water bath. The steam distillation of DFBN took 4 hours and was done to identify possible product loss if this process step were incorporated into the sequence instead of a phase cut. The DFBN distillate was separated from the water, melted, and collected in a tared sample bottle. The distillate weighed 403g and comprised 98.4 wt. % DFBN. The calculated yield of DFBN was 430g, which is a 93.6% yield based on DFBN starting material that was fed to the distillation vessel. The water distilled overhead was 1925g, and the water remaining in the distillation vessel was 117g. The total amount of water used in the steam distillation was 2042g. The distillation vessel contained a small amount (16g) of DFBN that was not distilled overhead. A small amount (17g) of a eutectic mixture of 80 wt. % DFBN and 16 wt. % CFBN was separated from the top of the solidified DFBN product jar.

Example 2- Fluorination of DCBN with KF 462g (330 mL) (3.32 moles) of DFBN and 285g (1.66 moles) of DCBN were charged to a 1000 mL 4-necked (Monel 400) cylindrical flask with 4 internal baffles. The flask was equipped with two condensers, a mechanical stirrer with two stacked agitators, and a thermowell. One condenser was installed between the reactor (flask) and the nitrogen bleed. 205g (3.5 moles) of KF were added to the reaction mixture after heating the pot to 170° C. The temperature controller was set at 170° C. and 4g of 18-crown-6 catalyst (0.5 wt. % based on the weight of DFBN and the reactants) was added. At the start of the reaction, the concentration of DCBN was about 38.3 wt. %. After 4 hours of reaction time, the DCBN concentration was 23.3 wt. %, CFBN concentration was 12.3 wt. %, and DFBN product concentration was 60 wt. %. The agitation speed was set at 300 rpm. After 18 hours of reaction time, the DCBN concentration was 5.5 wt. %, the CFBN concentration was 18.2 wt. %, and DFBN product concentration was 74.7 wt. %. The agitation speed was increased to 400 rpm. At 24 hours of reaction time, the DCBN concentration was 3.3 wt. %, the CFBN concentration was 16 wt. %, and DFBN product concentration was 78.3 wt. %. At 40 hours of reaction time, the DCBN concentration was 1.4 wt. %, the CFBN concentration was 14 wt. %, and DFBN product concentration was 82 wt. %. Agitation speed was increased to 1000 rpm and then slowed to 600 rpm, because the motor could not maintain the higher speed. At 48 hours of reaction time, the CFBN concentration was 3 wt. %, and DFBN product concentration was 93 wt. %, and 3.6g of 18-crown-6 catalyst was added, making for a total catalyst weight of 7.6g (1.02 wt. % based on DFBN plus the weight of the reactants). At 64 hours of reaction time, the CFBN concentration was 1.4 wt. %, and DFBN product concentration was 98 wt. %. The reaction products mixture was allowed to cool to 35° C. overnight.

The next day, the mixture was steam distilled as described in Example 1. All of the organic (DFBN) appeared to be distilled overhead in 2.5 hours. The resulting KCl/KF salt solution (brine) from the reactor was colored with a tan precipitate. The salt concentration was calculated at 30 wt. %. The DFBN distillate was separated from the water distillate, melted, and collected in a tared sample bottle. The DFBN distillate weighed 630.5g and had a purity of 98.4%. The weight of the water distilled overhead was 2592g. The total weight of the recovered DFBN was 626.7g (4.5 moles), and the total weight of the recovered CFBN was 10.2g (0.07 moles). The yield of DFBN and CFBN was 93% of theoretical.

Example 3: Fluorination of DCBN with KF 462g (3.32 moles) (330mL) of DFBN and 285g (1.66 moles) of DCBN were charged to a 1000 mL 4-necked (Monel 400) cylindrical flask with 4 internal baffles. The flask was equipped with two condensers, a mechanical stirrer with two stacked agitators, and a thermowell. One condenser was installed between the reactor (flask) and the nitrogen bleed. The temperature controller was set at 150° C. 205g (3.5 moles) of KF was added to the reaction mixture when the temperature reached 150° C. The reaction mixture was ground with a high speed grinder (18,000 rpm) for 2 minutes to reduce the size of the KF crystals. After the grinding, 10g of 18-crown-6 catalyst (1.0 mole % based on KF) was added. At the start of the reaction, the concentration of DCBN was about 38.3 wt. %. After 2 hours of reaction time, the DCBN concentration was 30.9 wt. %, CFBN concentration was 4.8 wt. % and DFBN product concentration was 63.1 wt. %, and the agitation speed was set at 500 rpm. After 18 hours of reaction time, the starting material was 14 wt. %, the CFBN concentration was 14 wt. %, and DFBN product concentration was 71.1 wt. %, and the agitation speed was set at 400 rpm. At 24 hours of reaction time, the DCBN concentration was 7.1 wt. %, the CFBN concentration was 17 wt. %, and DFBN product concentration was 75 wt. %. At 40 hours of reaction time, the DCBN concentration was 1.4 wt. %, the CFBN concentration was 9.7 wt. %, and DFBN product concentration was 87.8 wt. %. Agitation speed was increased to 1000 rpm and then slowed to 500 rpm because the motor could not maintain the higher speed. At 48 hours of reaction time, the CFBN concentration was 12 wt. %, and DFBN product concentration was 84.5 wt. %, and 2g of 18-crown-6 catalyst was added. At 64 hours of reaction time, the CFBN concentration was 8.4 wt. %, and DFBN product concentration was 90.3 wt. %. At 72 hours of reaction time, the CFBN concentration was 6.9 wt. %, and DFBN product concentration was 91 wt. %. At 88 hours of reaction time, the CFBN concentration was 4.5 wt. %, and DFBN product concentration was 94 wt. %. At 96 hours of reaction time, the CFBN concentration was 2.5 wt. %, and DFBN product concentration was 97.2 wt. %. At 120 hours of reaction time, the CFBN concentration was 2 wt. %, and DFBN product concentration was 98 wt. %.

The reaction mixture was allowed to cool to 45° C., 700 mL of water was then added, and the mixture was phase separated. The salt concentration of the resulting brine was 27 wt. %. The washed organic product was 645g of 98% pure DFBN (91.3% yield).

Example 4: Preparations:

The following methods and equipment were utilized in Example 4:

1. A glycol/water circulation bath pumped appropriately tempered solution through the distillation head, condenser and distillate receiver to avoid freezing of materials.

2. An overhead stirrer system for glassware comprised a polished glass stirrer shaft and an Ace TRUBORE Teflon stirrer bearing that comprised a Teflon inner bearing, nylon bushing and FETFE "O"-ring, nylon lock nut, Teflon saddle "O"-ring and Ace-Thread glass adapter. This setup was desired to withstand vacuum down to 0.1 mm and prevent leaking of volatile organics during the high temperature reaction.

3. Oven dried stainless steel tubes were provided in connection with the usage of a shaker table.

4. A prewarmed experimental tube reactor system was provided.

A 250mL, three neck, round bottom flask fitted with an overhead stirrer and jacketed distillation apparatus (vacuum jacketed, 10-tray Oldershaw column complete with jacketed splitter and distillate collection assembly) was charged with 42g of DFBN (as a melt). The contents were warmed to 60° C. after which 141g (0.9 mole) of CFBN, 86g (0.5 mole) of DCBN, 8.0g IPN (internal std), 9.1g (0.025 mole) of dibenzo-18-crown-6-crown ether catalyst and 65g (1.1 moles) of KF were added. The total mixture weight before distillation was 351.5g. Vacuum was applied to the system and the system pressure was slowly reduced to ≦10 Torr. While establishing the desired pressure, water was vigorously distilled from the system. Once the desired vacuum was established, the pot temperature was increased until the solution gently refluxed (a temperature of ≦110° C.). After the system was allowed to equilibrate through the 10-tray Oldershaw column, the reflux splitter, set at a 5:1 reflux ratio, was turned on and 36g of DFBN was collected overhead during the course of 2–3 hours. The total mixture weight after distillation was 316g. Atmospheric pressure was re-established with nitrogen, and the reaction mixture temperature was adjusted to 100° C. The mixture was then sampled and analyzed by liquid chromatography and checked for water using a Karl Fisher titrator, employing the following technique:

Two 15 cm disposable glass pipettes (with the tip broken off of one and a small plug of filter paper injected into the other) and a 20mL vial were heated to about 60° C. with a heat gun. The unbroken pipette was placed into the 20mL vial, close to the reaction set-up and the broken pipette was used to remove a 1–2mL sample from the mixture. The sample was quickly transferred into the unbroken pipette and the pipette, vial and solution were carried quickly to the titrator. A pipette bulb was used to push the warm solution through the plug of filter paper and pipette stem and four drops (60mg) of the liquid were added to the Aqnastar™ titrator.

Once the mixture was determined to be dry, the solution temperature was increased to 200° C. to allow the reaction to begin. During the course of the reaction, the mixture turned from light yellow to tan to light brown. Some KF and KCl salts formed a rind above the reaction mixture surface. The reaction mixture was periodically sampled and analyzed by liquid or gas chromatography, At the end of the reaction, the easily stirred mixture was cooled to 100° C. and was poured into a 1 liter, plastic separatory funnel preloaded with 250–500mL of water (preheated to 80° C.). The two phase mixture was shaken, and then the phases were allowed to separate for about 1–3 minutes. The bottom organic layer was then separated from the upper aqueous layer. A small rag layer was observed at the interface and was forwarded with the organic layer. Small pools of organic material were observed on top of the remaining tan colored aqueous layer. Once the separation was completed, both layers were assayed for organic content. The organic phase contained approximately 90g of DFBN, 130g of CFBN, 20g of DCBN, 9g of catalyst, 3g of various biaryl ether impurities and the internal standard. This organic mixture was then returned to the reaction vessel in preparation for the next cycle.

Example 5 Cycle No. 2

The organic material from the previous reaction in Example 4 was forwarded to a 250mL, three neck, round bottom flask fitted with an overhead stirrer and jacketed distillation apparatus (vacuum jacketed, 10-tray Oldershaw column complete with jacketed splitter and distillate collection assembly). The contents were warmed to 60° C. after which vacuum was applied to the system and the system pressure was slowly reduced to about 10 Torr and a portion of the DFBN produced in the previous reaction (73.5g, 0.52 mole) was removed by distillation. This distillation also effectively dried the system in preparation for the next charge of DCBN and KF. After removal of the DFBN product, vacuum was broken with nitrogen and DCBN (86g, 0.5 mole) and KF (65g, 1.1 moles) were charged to the reactor. The system was further dried by the vacuum distillation of residual DFBN and about 1 wt. % of the CFBN. Once dry (<100ppm water determined by use of the Karl Fisher titrator), the contents were heated to 200° C. for 18–24 hours. Once the reaction was completed, the reaction product mixture was worked up as described in Example 4 to remove the salts, and the organic phase contained approximately 70g DFBN, 120g CFBN, 40g DCBN, 9g catalyst, 6g of a mixture of three biaryl ether impurities and the internal standard.

Example 6: Simulation of 30 cycles (with respect to tars)

Tar material (a 20g mixture of fluorinated and chlorinated biaryl ethers) was combined with 200g (1.44 moles) of DFBN, 56g (0.326 mole) of DCBN, 41.6g (0.74 mole) of KF, 8.0g of dibenzo-18-crown-6 catalyst and internal standard in a 500mL, three neck round bottom flask fitted with an overhead stirrer and a jacketed distillation apparatus (vacuum jacketed, 10-tray Oldershaw column complete with jacketed splitter and distillate collection assembly). Approximately 50mL of DFBN was removed by vacuum distillation after which vacuum was broken with nitrogen and the mixture was heated to 200° C. for 14 hours. The mixture was then cooled to 60° C. and poured into 260g of water (preheated to 60° C.). The layers were separated and assayed for product. The organic layer contained 40.5g (0.29 mole) of additional DFBN, 49g (0.32 mole) of CFBN, 0g of DCBN, 8.0g of dibenzo-18-crown-6 catalyst, and 2.9g of additional biaryl ether tars.

Example 7: Use of Recovered Dibenzo-18-crown-6 Catalyst From Tar Purge Sequence

Recovered dibenzo-18-crown-6 catalyst (4.85g, 0.01 mole) was combined with a recycle organic mixture (28g DFBN, 56g CFBN, and 10g DCBN), additional DCBN (46.3g, 0.27 mole), KF (33g, 0.57 mole) and internal standard in a 250mL, three neck, round bottom flask fitted with an overhead stirrer and a jacketed distillation apparatus (vacuum jacketed, 10-tray Oldershaw column complete with jacketed splitter and jacketed distillate collection assembly).

Approximately 50mL of DFBN was removed by vacuum distillation after which vacuum was broken with nitrogen and the mixture was heated to 210°–220° C. for 11 hrs, cooled to 80° C., and washed as described in Example 6. The final organic layer contained approximately 25g (0.18 mole) of DFBN, 49g (0.32 mole) of CFBN, 12g (0.07 mole) of DCBN, 5.3g of dibenzo-18-crown-6 catalyst and 2.7g of biaryl ether tars.

Example 8: Catalyst Screening Examples

PART A: Apparatus Used in Screening Process

Several catalysts were screened using an Experimental Tube Reactor System. Sixteen tubes (½"× 3.125" with caps) sandwiched between two milled aluminum platens (9.125"× 10.25") were heated with four Chromalox® electric heating cartridges, two in each plate. The entire assembly was mounted on a shaker table (Eberback 6005 with explosion proof motor and 6040 utility box) for agitation, and the temperature was controlled using conventional devices. With this apparatus, sixteen catalysts/conditions could be screened in a single loading, thereby dramatically facilitating the screening process.

PART B: Method Used in Screening Process

Three tubes were assigned to each catalyst screened, and the tubes were loaded with the desired materials (DCBN, KF, catalyst, and DFBN). The fifteen tubes were placed between the milled aluminium platens and were heated at a predesignated temperature for 12 hours. One tube was then pulled from each set, after which the remaining tubes were heated for an additional 12 hours at a second predesignated (higher) temperature. At the end of this cycle, a second tube was pulled from each set and the remaining tubes were heated at a third (higher) predesignated temperature for a final 12 hours. The final tubes were pulled at the end of this cycle. The product mixture in each tube was dissolved into acetonitrile to allow the KCl and residual KF to precipitate. A sample of the resulting acetonitrile solution was then analyzed by liquid or gas chromatography.

PART C: Example of Catalyst Run in Tubular Reactor (Drying Precautions and Internal Standard)

206g of DFBN and 64g of KF were charged into a clean, 500mL, three neck round bottom flask fitted with an overhead stirrer and a 15 tray Oldershaw column with a vacuum distillation head. 36g of DFBN was then distilled overhead at a 5:1 reflux ratio (1 over, 5 back to pot) at 100° C. (10 Torr). Once completed, vacuum was released and a pot sample was filtered and titrated to determine the amount of water present by Karl Fisher titrator (results were consistently <100ppm $H_2O$). To this solution was added the internal standard (IPN, 6.42g) and DCBN (86g). A pot sample was again taken and titrated for water using the Karl Fisher titrator (it was important to preheat the pipettes to about 50° C. prior to taking a sample in order to prevent the sample from freezing prior to its injection into the Karl Fisher titrator). This master batch was used in all of the quantitative screening studies described in this Example. The tubes were prepared as described below:

Two clean stainless steel tubes with endcaps were individually weighed and tared after which each was charged with 2.5–5 mole % of catalyst. A 5mL aliquot (about 5.5g) of the above prepared pot solution was then piperted into each tube (the solution and wide-bore pipettes had to be warm in order to prevent freezing on the walls of the pipettes during the transfer). The tubes were capped and the caps were tightened to about 40 lbs using a torque wrench and vise. The tubes were weighed again and one tube from each set was placed in the Tubular Reactor System along with 6 similarly prepared tubes (different catalysts or blanks). The tubes were heated to 200° C. for 12 hrs after which they were removed and replaced with the second tube of each set. The second set of tubes was heated to 220° C. for 12 hours, cooled and removed. The tubes were cooled and weighed to ensure no leakage had occurred. Each tube was then opened and acetonitrile was added to help slurry the contents. The contents were emptied into a 20mL vial, making sure that all material was removed from the tube during workup. The KF was allowed to settle and an aliquot was diluted in acetonitrile and injected into the gas chromatograph. Another aliquot was diluted in a 40 wt. % aqueous solution of acetonitrile which was injected into the liquid chromatograph. The components from each product mixture were then quantified using Response Factor Information.

| PART D: Catalysts Examined: | | | | | |
|---|---|---|---|---|---|
| | CROWN COMPOUNDS | | | | |
| *CATALYST | TIME | TEMP. | % Conversion | wt. % DFBN | wt. % CFBN |
| Dibenzo | 12 hr | 180° C. | 76.16 | 36.54 | 28.57 |
| 18-C-6 | 12 hr | 200° C. | 90.49 | 40.31 | 31.21 |
| | 12 hr | 220° C. | 98.07 | 54.19 | 24.93 |
| 12-C-4 | 12 hr | 180° C. | 56.58 | 34.79 | 13.75 |
| | 12 hr | 200° C. | 77.57 | 36.25 | 26.47 |
| | 12 hr | 220° C. | 72.02 | 33.87 | 24.68 |
| 15-C-5 | 12 hr | 180° C. | 87.99 | 40.14 | 31.22 |
| | 12 hr | 200° C. | 94.52 | 42.19 | 28.76 |
| | 12 hr | 220° C. | 95.85 | 44.93 | 28.15 |
| Dicyclohexano 18-C-6 | 12 hr | 180° C. | 89.51 | 39.17 | 30.00 |
| | 12 hr | 200° C. | 97.60 | 48.62 | 23.79 |
| | 12 hr | 220° C. | 98.89 | 54.07 | 20.79 |
| 18-C-6 | 12 hr | 180° C. | 89.45 | 50.03 | 37.32 |
| | 12 hr | 200° C. | 97.75 | 55.29 | 27.07 |

PART D: Catalysts Examined:

| | 12 hr | 220° C. | 99.90 | 52.23 | 18.60 |

*Respectively known as:
Dibenzo 18-C-6 = Dibenzo (B,K) (1,4,7,10,13,16)hexaoxacyclooctadecin: 6,7,9,10,17,18,20,21-octahydro-;
12-C-4 = 1,4,7,10-tetraoxacyclododecane;
15-C-5 = 1,4,7,10,13-pentaoxacyclopentadecane;
Dicyclohexano-18-C-6 = 2,5,8,15,18,21-hexaoxatricyclo (20.4.0.09,14)hexacosane;
18-C-6 = 1,4,7,10,13,16-hexaoxacyclooctadecane.

AMMONIUM SALTS

| *CATALYST | TIME | TEMP. | % Conversion | wt. % DFBN | wt. % CFBN |
|---|---|---|---|---|---|
| Ph(CH$_3$)$_3$NCl | 12 hr | 180° C. | 51.43 | 33.88 | 13.89 |
| | 12 hr | 200° C. | 77.10 | 35.26 | 27.54 |
| | 12 hr | 220° C. | 85.11 | 35.55 | 28.15 |
| (C$_5$H$_{11}$)$_4$NBr | 12 hr | 180° C. | 69.39 | 32.22 | 24.20 |
| | 12 hr | 200° C. | 80.16 | 38.43 | 28.32 |
| | 12 hr | 220° C. | 85.72 | 39.62 | 32.19 |
| Aliquat 336* | 12 hr | 180° C. | 88.22 | 35.58 | 32.17 |
| | 12 hr | 200° C. | 89.03 | 34.54 | 30.86 |
| | 12 hr | 220° C. | 92.04 | 36.07 | 30.11 |
| (C$_{12}$H$_{25}$)Me$_3$NBr | 12 hr | 180° C. | 92.26 | 43.97 | 31.70 |
| | 12 hr | 200° C. | 94.68 | 45.30 | 26.95 |
| | 12 hr | 220° C. | 94.47 | 47.92 | 27.28 |
| CH$_3$(CH$_2$)$_{13}$N(CH$_3$)$_3$Br | 12 hr | 180° C. | 91.02 | 37.62 | 32.11 |
| | 12 hr | 200° C. | 91.44 | 38.35 | 26.36 |
| | 12 hr | 220° C. | 94.33 | 28.89 | 48.06 |
| ARQUAD 16/60 | 12 hr | 180° C. | 68.37 | 21.82 | 26.96 |
| (C$_{16}$H$_{33}$)N(CH$_3$)$_3$Br | 12 hr | 200° C. | 75.19 | 17.17 | 26.42 |
| | 12 hr | 220° C. | 73.67 | 18.79 | 26.52 |

*Respectively known as:
phenyl trimethyl ammonium chloride
tetrapentylammonium bromide
Aliquat 336 = 1-octanaminium: N-methyl-N,N-dioctil-, chloride or trioctylmethylammonium chloride;
dodecyltrimethylammonium bromide;
tetradecyltrimethylammonium bromide;
Arquad 16/60 = hexadecyltrimethylammonium bromide.

PHOSPHONIUM SALTS

| *CATALYST | TIME | TEMP. | % Conversion | wt. % DFBN | wt. % CFBN |
|---|---|---|---|---|---|
| (1-NAPHTHYLMETHYL) Ph$_3$PCl | 12 hr | 180° C. | 40.02 | 32.03 | 1.73 |
| | 12 hr | 200° C. | 47.15 | 29.33 | 5.05 |
| | 12 hr | 220° C. | 58.60 | 29.79 | 16.37 |
| (METHOXYMETHYL) Ph$_3$PCl | 12 hr | 180° C. | 42.55 | 28.28 | 1.33 |
| | 12 hr | 200° C. | 51.25 | 33.27 | 12.06 |
| (3-NITROBENZYL) Ph$_3$PBr | 12 hr | 180° C. | 39.63 | 31.65 | 1.97 |
| | 12 hr | 200° C. | 46.68 | 34.95 | 5.35 |
| | 12 hr | 220° C. | 56.95 | 25.20 | 11.29 |
| Ph$_4$PCl | 12 hr | 180° C. | 47.69 | 26.14 | 5.77 |
| | 12 hr | 200° C. | 56.75 | 26.86 | 11.57 |
| | 12 hr | 220° C. | 64.96 | 27.04 | 19.92 |

*Respectively known as:
1-naphthylmethyltriphenylphosphonium chloride;
methoxymethyltriphenylphosphonium chloride;
3-nitrobenzyltriphenylphosphonium bromide;
tetraphenylphosphonium chloride.

LINEAR POLYETHERS

| *CATALYST | TIME | TEMP. | % Conversion | wt. % DFBN | wt. % CFBN |
|---|---|---|---|---|---|
| IGEPAL CO-990 | 12 hr | 180° C. | 63.64 | 28.02 | 23.94 |
| | 12 hr | 200° C. | 80.58 | 33.20 | 31.07 |
| | 12 hr | 220° C. | 93.52 | 43.81 | 31.54 |
| BRIJ 30 | 12 hr | 180° C. | 39.97 | 33.85 | 02.51 |
| | 12 hr | 200° C. | 50.49 | 32.96 | 10.74 |
| | 12 hr | 220° C. | 61.80 | 30.87 | 18.93 |
| IGEPAL CA 520 | 12 hr | 180° C. | 40.34 | 34.54 | 02.60 |
| | 12 hr | 200° C. | 59.84 | 34.36 | 16.15 |
| | 12 hr | 220° C. | 57.12 | 34.18 | 14.31 |
| HEPTA EG MDE | 12 hr | 180° C. | 41.71 | 32.64 | 04.84 |
| | 12 hr | 200° C. | 49.41 | 32.66 | 10.11 |
| | 12 hr | 220° C. | 59.10 | 31.68 | 17.96 |
| TRITON X-114 | 12 hr | 180° C. | 40.46 | 33.90 | 04.30 |

-continued

PART D: Catalysts Examined:

| | 12 hr | 200° C. | 49.66 | 33.60 | 11.26 |
|---|---|---|---|---|---|
| | 12 hr | 220° C. | 63.77 | 33.33 | 23.21 |
| NONA EG MDE | 12 hr | 180° C. | 47.85 | 34.07 | 07.77 |
| | 12 hr | 200° C. | 47.26 | 32.93 | 08.06 |
| | 12 hr | 220° C. | 69.77 | 31.54 | 24.27 |
| IGEPAL CA 210 | 12 hr | 180° C. | 38.04 | 35.90 | 0 |
| | 12 hr | 200° C. | 64.76 | 53.82 | 06.48 |
| | 12 hr | 220° C. | 37.66 | 31.76 | 09.55 |
| IGEPAL CA 720 | 12 hr | 180° C. | 57.41 | 29.36 | 18.10 |
| | 12 hr | 200° C. | 74.50 | 32.48 | 27.91 |
| | 12 hr | 220° C. | 83.93 | 34.74 | 31.48 |
| POLYGLY-4000 | 12 hr | 180° C. | 43.34 | 33.47 | 05.00 |
| | 12 hr | 200° C. | 53.78 | 33.58 | 12.59 |
| | 12 hr | 220° C. | 69.13 | 35.09 | 23.88 |
| POLYGLY-E 3350 NF | 12 hr | 180° C. | 53.85 | 32.63 | 12.84 |
| | 12 hr | 200° C. | 73.24 | 33.10 | 24.47 |
| | 12 hr | 220° C. | 89.51 | 38.89 | 30.35 |
| TRITON X-114 | 12 hr | 180° C. | 40.46 | 33.90 | 04.30 |
| | 12 hr | 200° C. | 49.68 | 33.60 | 11.28 |
| | 12 hr | 220° C. | 63.77 | 33.33 | 23.21 |
| TETRA EG D1-P-Tocylate | 12 hr | 180° C. | 40.26 | 33.25 | 02.31 |
| | 12 hr | 200° C. | 46.82 | 27.81 | 06.92 |
| | 12 hr | 220° C. | 49.45 | 30.11 | 06.52 |
| TETRA EG DME | 12 hr | 180° C. | 44.88 | 34.71 | 04.76 |
| | 12 hr | 200° C. | 60.53 | 23.85 | 18.99 |
| | 12 hr | 220° C. | 74.20 | 18.93 | 23.52 |
| NONA EG DME | 12 hr | 180° C. | 39.36 | 31.17 | 04.40 |
| | 12 hr | 200° C. | 61.14 | 31.01 | 19.15 |
| | 12 hr | 220° C. | 64.91 | 30.24 | 23.45 |
| POLYGLY-E 4500 NF | 12 hr | 180° C. | 85.56 | 34.40 | 15.55 |
| | 12 hr | 200° C. | 81.30 | 39.04 | 30.40 |
| | 12 hr | 220° C. | 93.84 | 46.00 | 31.31 |
| TETRA EG-BIS(9-Chinelyl)E | 12 hr | 180° C. | 69.88 | 28.08 | 25.50 |
| | 12 hr | 200° C. | 82.90 | 25080 | 29.91 |
| | 12 hr | 220° C. | 94.80 | 36.20 | 27.08 |

*Respectively known as:
Igepal Co-990 = (nonylphenoxypolyethylene oxide);
Brij 30 = poly (oxy-1,2-ethanediyl), .alpha.-dodecyl-.omega.-hydroxy-;
Igepal CA 520 = poly(oxy-1,2-ethanediyl), .alpha.-[(1,1,3,3-tetramethylbutyl)phenyl]-.omega.-hydroxy-(avg. mol. wt. = 520);
Heptaethyleneglycol-monododecylether;
Triton x-114 = Polyglycol E-350, 4-(1,1,3,3-tetramethylbutyl)phenylether;
Nonoethyleneglycol monododecylether;
Igepal CA 210;
Igepal CA 720 = Same as Igepal CA 520 except higher avg. mol. wt.;
Polyethylene glycol-4000 avg. mol. wt.;
Polyethylene glycol-3350 avg. mol. wt. non-food grade;
Triton X-114 = See above;
Tetraethyleneglycol di-p-tosylate;
Tetraethyleneglycol dimethylether;
nonaethyleneglycol dimethylether;
polyethyleneglycol-4500 avg. mol. wt., non-food grade;
Tetraethyleneglycol bis(8-chinonyl)ether.

NF — Non Food Grade;
EG — Ethylene glycol;
Ph — phenyl;
Me — methyl.

Example 9: Dibenzo-18-Crown-6 Crown Ether Catalyst Recovery Using Steam Stripping (Steam Distillation) for Recovery of Benzonitrile Compounds and Using Methanol as a Solvent A 195g sample of an actual reaction product mixture was obtained. The DB-18, partially converted CFBN, and the tars in this mixture had been recycled through three halide exchange reactions. The table provided below gives the assay and weights of this reaction mixture.

| Actual Reaction Mixture used for DB-18 Recovery | | |
|---|---|---|
| COMPONENT | WT % (LC Assay) | GRAMS |
| DFBN | 28.4 | 55.3 |
| CFBN | 46.6 | 90.9 |
| DCBN | 14.2 | 27.7 |
| INSIT. STD. | 3.0 | 5.9 |
| DB-18 | 3.1 | 6.0 |
| TARS | 4.7 | 9.2 | where LC = Liquid Chromatography 161g of benzonitriles were steam stripped from the reaction product mixture, leaving a dark fluid oil phase on the bottom of a fairly clear water phase. 28.6g of stripped organics (the bottom organic phase) were decanted into a flask containing 250g of methanol. The tar was extracted for 3 hours at 20° C. with agitation supplied by a magnetic stir bar. The catalyst phase was filtered, washed with about 10 grams of methanol, and dried. The methanol was evaporated from the filtrate and rinse. The recovered catalyst weighed 5.1g and assayed at 98.2 wt. %. The dried filtrate residue weighed 23g and contained about 4.5 wt. % DB-18. The estimated catalyst recovery was about 83 wt. % by both the cake and the filtrate calculation. The quality of the recovered catalyst was verified by using it in a subsequent halide exchange reaction, see Example 7. Both the kinetics and yield were found to be substantially the same as when virgin catalyst was used.

Example 10: Dibenzo-18-Crown-6 Crown Ether Catalyst Recovery Using Vacuum Distillation of Benzonitrile Compounds in a Distillation System Comprising a Column A synthetic mixture of 15g of pure dibenzo-18-crown-6 catalyst obtained from Aldrich Chemicaland 41.4g of tars (fluorinated and chlorinated biaryl ethers) was added to 80g of a mixture of DFBN and CFBN. This mixture was added to a three neck, round bottom flask fitted with an overhead stirrer and jacketed distillation apparatus (vacuum jacketed, 10-tray Oldershaw column complete with jacketed splitter and distillate collection assembly). The pressure was reduced to about 5 mm HG absolute pressure and the benzonitriles were distilled off with heat. During the experiment, it became obvious that due to column holdup, a significant amount of benzonitriles would drain back into the distillation flask when the vacuum was relieved. In an attempt to minimize this, nitrogen was bled into the distillation flask to help sweep the column. It appeared that the majority of benzonitriles had been distilled when the pot reached about 230° C. An estimated 5 to 10 grams of benzonitriles drained back into the pot. The distillation bottoms (about 54g) was cooled to about 120° C. and then transferred into 350g of solvent comprising 96 wt. % methanol, 3 wt. % acetone, and 1 wt. % water. The slurry was agitated for about 2 hours, then filtered, washed with 50g of methanol, and then dried. The filtrates were also evaporated to dryness. The resulting dry cake weighed 30.1g and assayed at 60.2 wt. % catalyst. The filtrate weighed 20.2g and contained 3.7 wt. % catalyst for an estimated catalyst recovery of 96 wt. %. The low catalyst purity was likely due to the tar which was used for this experiment. Liquid chromatography chromatograms showed a significantly higher level of later-eluting tars than what is typical of the tars expected to be generated in making DFBN according to the invention. These later elutes may have been trimers and tetramers of biaryl ethers (i.e., higher molecular weight tars). Such higher molecular weight tars tend to be less soluble in methanol than the tars expected to be generated in making DFBN according to the invention.

It is believed that contamination of the concentrated tars at high temperature may lead to formation of some of the higher molecular weight tars. Therefore, a tight distillation system would be preferred in scaling up this method of recovery. Also, it may be desirable to install a trap at the base of the column to collect the benzonitriles held up in the column or allow them to drain to another vessel. This would prevent unnecessary losses of benzonitriles to the tar purge stream.

Of course, it should be understood that a wide range of changes and modifications can be made to the preferred embodiments described above including the individual catalysts used in the examples. The process of this invention is not limited to the examples listed above, but can include should be interpreted by the teachings within the detailed description herein. It is therefore intended that the foregoing description be regarded as illustrative rather than limiting, and that it be understood that it is the following claims, including all equivalents, which are intended to define the scope of this invention.

What is claimed is:

1. A process for making 2,6-difluorobenzonitrile, comprising:
   a) reacting 2,6-dichlorobenzonitrile with a substantially anhydrous alkali metal fluoride in a reactor at a temperature between about 160° C. and about 300° C. and in the presence of a phase transfer catalyst but in the absence of a solvent, to produce a first mixture comprising 2-chloro-6-fluorobenzonitrile, 2,6-difluorobenzonitrile, unreacted 2,6-dichlorobenzonitrile, the catalyst and tars resulting from the reaction;
   b) separating 2,6-difluorobenzonitrile from the first mixture to produce a second mixture comprising 2-chloro-6-fluorobenzonitrile, 2,6-dichlorobenzonitrile, the tars, and the catalyst; and
   c) separating 2,6-dichlorobenzonitrile and 2-chloro-6-fluorobenzonitrile from the second mixture to produce a third mixture comprising the tars and the catalyst and recycling the separated 2,6-dichlorobenzonitrile and 2-chloro-6-fluorobenzonitrile into the reactor.

2. The process of claim 1 wherein the reaction is conducted at about ambient pressure.

3. The process of claim 1 wherein the reaction temperature is between about 190° C. and about 260° C.

4. The process of claim 3 wherein the reaction temperature is about 225° C.

5. The process of claim 1 wherein the phase transfer catalyst is selected from the group consisting of polyethers, tetra-substituted phosphonium salt, tetra-substituted ammonium salt and cryptand.

6. The process of claim 5 wherein the polyether catalyst is a crown ether or a linear polyether.

7. The process of claim 6 wherein the crown ether catalyst is selected from the group consisting of 18-crown-6 crown ether, 15-crown-5 crown ether, dibenzo-18-crown-6 crown ether and dicyclohexano 18-crown-6 ether.

8. The process of claim 5 wherein the ammonium salt is selected from the group consisting of phenyl trimethyl ammonium chloride, tetrapentylammonium bromide, trioctylmethylammonium chloride, dodecyltrimethylammonium bromide, tetradecyltrimethylammonium bromide, or hexadecyltrimethylammonium bromide.

9. The process of claim 5 wherein the phosphonium salt is selected from the group consisting of 1-naphthylmethyl triphenyl phosphonium chloride, methoxymethyl triphenyl phosphonium chloride, 3-nitrobenzyl triphenyl phosphonium chloride and tetraphenyl phosphonium chloride.

10. The process of claim 1 wherein the metal fluoride is selected from the group consisting of sodium fluoride, cesium fluoride, potassium fluoride, rubidium fluoride and cuprous fluoride.

11. The process of claim 1 wherein the metal fluoride is potassium fluoride.

12. The process of claim 1 further comprising extracting the tars from the third mixture using a solvent selected from the group consisting of methanol, acetone, acetonitrile, toluene and chlorobenzenes.

13. The process of claim 12 further comprising recovering the catalyst after the tar extraction.

14. The process of claim 13 further comprising recycling the recovered catalyst into the reactor.

15. A process for making 2,6-difluorobenzonitrile, comprising:
   a) preparing a first mixture in a reactor at a temperature not greater than about 130° C. in the absence of a solvent, the first mixture comprising a crown ether or linear polyether, 2,6-dichlorobenzonitrile, a substantially anhydrous metal fluoride, and one or more benzonitrile compounds selected from the group consisting of 2-chloro-6-fluorobenzonitrile and 2,6-difluorobenzonitrile;
   b) distilling off up to about 75 weight percent of the DFBN and/or CFBN compounds present in the first mixture to dry the first mixture, thereby producing a second mixture;
   c) increasing the temperature of the second mixture to between about 160° C. and about 300° C. to produce a third mixture comprising 2,6-difluorobenzonitrile, 2-chloro-6-fluorobenzonitrile, 2,6-dichlorobenzonitrile, tars resulting from the reaction, and the catalyst; and
   d) separating 2,6-difluorobenzonitrile from the third mixture to produce a fourth mixture comprising 2-chloro-6-fluorobenzonitrile, 2,6-dichlorobenzonitrile, the tars, and the catalyst.

16. The process of claim 15 wherein the reaction is conducted at about ambient pressure.

17. The process of claim 15 wherein the temperature in step c) is between about 190° C. and about 260° C.

18. The process of claim 17 wherein the temperature in step c) is about 225° C.

19. The process of claim 15 wherein the crown ether catalyst is selected from the group consisting of 18-crown-6 crown ether, 15-crown-5 crown ether, 12-C-4 crown ether, dibenzo-18-crown-6 crown ether and dicyclohexano 18-crown-6 ether.

20. The process of claim 15 wherein the metal fluoride is selected from the group consisting of sodium fluoride, cesium fluoride, potassium fluoride, rubidium fluoride and cuprous fluoride.

21. The process of claim 15 wherein the metal fluoride is potassium fluoride.

22. The process of claim 15 further comprising separating 2,6-dichlorobenzonitrile and 2-chloro-6-fluorobenzonitrile from the fourth mixture to produce a fifth mixture comprising the tars and the catalyst.

23. The process of claim 22 wherein the tars are extracted from the fifth mixture using a solvent selected from the group consisting of methanol, acetone, acetonitrile, toluene and chlorobenzenes.

24. The process of claim 23 wherein the catalyst is recovered after the tar extraction.

25. The process of claim 24 wherein the recovered catalyst is recycled into the reactor.

\* \* \* \* \*